United States Patent
Bellamkonda et al.

(10) Patent No.: US 8,652,215 B2
(45) Date of Patent: Feb. 18, 2014

(54) NANOFILAMENT SCAFFOLD FOR TISSUE REGENERATION

(75) Inventors: Ravi V. Bellamkonda, Marietta, GA (US); Young-Tae Kim, Arlington, TX (US); Satish Kumar, Lawrenceville, GA (US); Dasharatham Goud Janagama, Tucker, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1148 days.

(21) Appl. No.: 11/817,923

(22) PCT Filed: Mar. 7, 2006

(86) PCT No.: PCT/US2006/008325
§ 371 (c)(1), (2), (4) Date: Sep. 6, 2007

(87) PCT Pub. No.: WO2006/096791
PCT Pub. Date: Sep. 14, 2006

(65) Prior Publication Data
US 2008/0208358 A1    Aug. 28, 2008

Related U.S. Application Data

(60) Provisional application No. 60/659,218, filed on Mar. 7, 2005.

(51) Int. Cl.
*A61F 2/02*    (2006.01)

(52) U.S. Cl.
USPC .................................. 623/23.72; 623/23.76

(58) Field of Classification Search
USPC .......................................... 623/23.72, 23.76
See application file for complete search history.

(56) References Cited

U.S. PATENT DOCUMENTS

| | | | |
|---|---|---|---|
| 4,552,707 A * | 11/1985 | How | 264/441 |
| 4,892,552 A | 1/1990 | Ainsworth et al. | |
| 5,053,453 A | 10/1991 | Ku | |
| 5,217,492 A | 6/1993 | Guire et al. | |
| 5,916,585 A | 6/1999 | Cook et al. | |
| RE36,370 E | 11/1999 | Li | |
| 6,303,136 B1 | 10/2001 | Li et al. | |
| 6,309,423 B2 | 10/2001 | Hayes | |
| 6,347,930 B1 | 2/2002 | Muscat et al. | |
| 6,716,225 B2 | 4/2004 | Li et al. | |
| 7,214,242 B2 | 5/2007 | Abraham et al. | |

(Continued)

OTHER PUBLICATIONS

Bini, et al., "Peripheral Nerve Regeneration by Microbraided Poly (L-lactide-co-glycolide) Biodegradable Polymer Fibers." Journal of Biomedical Materials Research A, 68: 286-305 (2003).

(Continued)

*Primary Examiner* — Gregory Anderson
(74) *Attorney, Agent, or Firm* — Sutherland Asbill & Brennan LLP

(57) ABSTRACT

A scaffold for tissue regeneration is provided. In a preferred embodiment, the scaffold is implantable in a patient in need of nerve or other tissue regeneration and includes a structure which has a plurality of uniaxially oriented nanofibers made of at least one synthetic polymer. Preferably, at least 75% of the nanofibers are oriented within 20 degrees of the uniaxial orientation. The scaffold beneficially provides directional cues for cell and tissue regeneration, presumably by mimicking the natural strategy using filamentous structures during development and regeneration.

23 Claims, 4 Drawing Sheets

(56) References Cited

U.S. PATENT DOCUMENTS

| | | | |
|---|---|---|---|
| 7,374,774 | B2 | 5/2008 | Bowlin et al. |
| 7,481,788 | B2 | 1/2009 | Naimark et al. |
| 7,531,503 | B2 | 5/2009 | Atala et al. |
| 7,615,373 | B2 * | 11/2009 | Simpson et al. ............... 435/398 |
| 7,622,299 | B2 | 11/2009 | Sanders et al. |
| 2003/0175410 | A1 | 9/2003 | Campbell et al. |
| 2003/0211130 | A1 | 11/2003 | Sanders et al. |
| 2004/0052861 | A1 | 3/2004 | Hatcher et al. |
| 2005/0038498 | A1 | 2/2005 | Dubrow et al. |
| 2005/0095695 | A1 | 5/2005 | Shindler et al. |
| 2005/0187162 | A1 | 8/2005 | Dhanaraj et al. |
| 2006/0085063 | A1 | 4/2006 | Shastri et al. |
| 2007/0269481 | A1 | 11/2007 | Li et al. |
| 2008/0220042 | A1 | 9/2008 | Hashi et al. |

OTHER PUBLICATIONS

Dubey, et al., "Guided Neurite Elongation and Schwann Cell Invasion into Magnetically Aligned Collagen in Simulated Peripheral Nerve Regeneration." Experimental Neurology, 158: 338-50 (1999).
Hatton, Paul V., "Tissue Engineering of Human Cartilage-Spider Silk and other Scaffolds." Centre for Biomaterial and Tissue Engineering at the University of Sheffield. From molecules to patients conference, Jun. 9, 2005 <http://www.cbte.group.shetac.uk/news/abstracts/hatton/html> (abstract).
Li, et al., "Electrospinning Nanofibers as Uniaxially Aligned Arrays and Layer-by-Layer Stacked Films." Advanced Materials, 16(4): 361-66 (2004).
Ma, Peter X., "Polymeric Biomaterials and Tissue Engineering Lab."
Ngo, et al., "Poly (L-lactide) Microfilaments Enhance Peripheral Nerve Regeneration Across Extended Nerve Lesions." Journal of Neuroscience Research, 72: 227-38 (2003).
Oest, et al., "Oriented Porous Polymer Scaffolds Promote Vascularized Repair of Critically-Sized Bone Defects in Vivo." Regenerate, Jun. 1-3, 2005 <http://www.regenerate-online.com/abstract_Oest.html> (abstract).
Rangappa, et al., "Laminin-coated Poly (L-lactide) Filaments Induce Robust Neurite Growth While Providing Directional Orientation." Journal of Biomedical Materials Research A, 51: 625-34 (2000).
"Scaffolds for Developing 3D Tissues." Centre for Biomaterial and Tissue Engineering at the University of Sheffield, <http://www.cbte.group.shef.ac.uk/research/mat5.html>.
Xu, et al., "Aligned Biodegradable Nanofibrous Structure: A Potential Scaffold for Blood Vessel Engineering." Biomaterials, vol. 25, Issue 5, Feb. 2004, pp. 877-886.
He, et al., Fabrication of Collagen-Coated Biodegradable Polymer Nanofiber Mesh and Its Potential for Endothelial Cells Growth. Biomaterials, 2005, vol. 26, pp. 7606-7615, Abstract, Section 3.1, figures.
International Search Report of PCT/US06/08325.
Office Action mailed Mar. 23, 2010 for U.S. Appl. No. 11/668,448 (U.S. Publication No. 2007/0279481).
Office Action mailed Oct. 13, 2010 for U.S. Appl. No. 11/811,923 (U.S. Publication No. 2008/0220042).
Yang, F. et al., "Eletrospinning of nano/micro scale poly9L-lactic acid) aligned fibers and their potential in neuraltissue engineering", Biomaterials (2005) vol. 26, No. 15, pp. 2603-2610.
Zuwei, M. et al., "Grafting of gelatin on electrospun poly(caprolacton) nanofibers to improve endothelial cell spreading and proliferation and to control cell orientation", Tissue Engineering (Jul.-Aug. 2005), vol. 11, No. 7-8, pp. 1149-1158.

* cited by examiner 3D construct of hydrogel layer and nanofilaments layer.

NANOFILAMENT SCAFFOLD FOR TISSUE REGENERATION

CROSS REFERENCE TO RELATED APPLICATIONS

This application claims benefit of U.S. Provisional Application No. 60/659,218, filed Mar. 7, 2005. That application is incorporated herein by reference in its entirety.

STATEMENT REGARDING FEDERALLY SPONSORED RESEARCH OR DEVELOPMENT

This invention was made with U.S. government support under Contract No. EEC-9731643 awarded by the National Science Foundation and under Contract No. R01NS044409-02 awarded by the National Institutes of Health. The U.S. government has certain rights in the invention.

BACKGROUND OF THE INVENTION

This invention is generally in the field of tissue engineering, and more particularly pertains to synthetic scaffold materials and methods useful in directing tissue growth in vivo or ex vivo.

Severe traumatic injury or invasive surgical procedures on a peripheral nerve can result in a gap between two nerve stumps. The clinical "gold standard" for bridging peripheral nerve gaps is the use of autografts, typically, the sensory sural nerve. However, the use of autografts is limited by the inadequate availability of nerves to use in the autograft (IJkema-Paassen, et al., *Biomaterials* 25:1583-92 (2004)), the lack of co-adaptation between the injured nerve and the nerve graft due to size/length/modality mismatch (Nichols, et al., *Exp. Neurol.* 190:347-55 (2004)), and functional loss at the donor sites (Bini, et al., *J. Biomed. Mater. Res A* 68:286-95 (2004)). Moreover, complications at the donor site such as numbness, hyperesthesia, or formation of painful neuroma also have to be addressed (Itoh, et al., *Biomaterials* 23:4475-81 (2002); Matsuyama, et al., *Neurol. Med. Chir.* (Tokyo) 40:187-99 (2000)). Therefore, it is imperative that alternative approaches that are ready-to-use, pre-customized for reducing the mismatch, and suitable for both sensory and motor nerve regeneration are developed.

Many research and development efforts are focused on manipulating cell growth, proliferation, and differentiation to repair or replace damaged tissue structures in the body, or to grow tissues and organs. One approach is the use of engineered tissue scaffolds.

Tubular nerve conduits have been used clinically for repairing peripheral nerve injury (Taras, et al., *J. Hand Ther.* 18:191-97 (2005)). These nerve conduits, which are made of non-porous silicone or porous natural/synthetic polymers, bridge the injured nerve stumps and help form a fibrin cable which provides a substrate for the ingrowth of Schwann cells and other cells such as fibroblasts. The infiltrating Schwann cells reorganize to create longitudinally oriented bands of Bungner, which serve as a guiding substrate and a source of neurotrophic factors to foster axonal regrowth (Bungner, 1891; Ide, *Neurosci Res.* 25:101-21 (1996)). However, these approaches are limited in their ability to enable regeneration across long nerve gaps, and have been unsuccessful in promoting regeneration across gaps longer than 15 mm in rodents. Failure of nerve regeneration across long gaps, i.e., those greater than 15 mm, seems to be the result of a lack of the formation of an initial fibrin cable, which is necessary for the formation of the bands of Bungner (Lundborg, et al., *Exp. Neuro.* 76:361-75 (1982)).

Conventional tissue engineering scaffolds are isotropic and provide no directional cues to promote directional cell and tissue growth and regeneration, and require the addition of exogenously delivered neurotrophic factors to increase the intrinsic growth capacity of injured axons. Accordingly, there exists a need to develop a scaffold that promotes directional cell and tissue growth and regeneration across long nerve gaps. More generally, there exists a need to develop an engineered scaffold that promotes directional cell and tissue growth and regeneration for use in a variety of applications, such as cartilage, bone, neural, and cardiovascular tissue engineering.

SUMMARY OF THE INVENTION

An improved scaffold for tissue regeneration has been developed. In one aspect, a scaffold is provided that includes a structure comprising a plurality of uniaxially oriented nanofibers made of at least one synthetic polymer. In a preferred embodiment, at least 75% of the nanofibers are oriented within 20 degrees of the uniaxial orientation. In one embodiment, the nanofibers have a diameter between about 400 nm and about 1000 nm. In a preferred embodiment, the tissue scaffold is implantable scaffold and the structure comprises two or more stacked layers of the uniaxially oriented nanofibers, the layers being oriented such that the nanofiber orientation of among the layers is substantially identical. In one embodiment, the structure further includes at least one spacer between layers of uniaxially oriented nanofibers in the stacked layers. In one case, the spacer has a thickness between 50 and 250 µm. The space may include a hydrogel, polyethylene glycol, agarose, alginate, polyvinyl alcohol, collagen, Matrigel, chitosan, gelatin, or a combination thereof. For example, the structure may include alternating layers of oriented nanofibers and layers of hydrogel. In one embodiment, the implantable scaffold further includes a tubular conduit in which the structure is disposed.

The synthetic polymer of the implantable scaffold may be biodegradable or non-biodegradable, or a combination (e.g., mixture) of these types of polymers. Examples of suitable biodegradable polymers include poly(caprolactone), poly(lactic-co-glycolic acid), poly(lactic acid), or a combination thereof. An example of a suitable non-biodegradable polymer is poly(acrylonitrile).

In one embodiment, the implantable scaffold further includes at least one bioactive agent. In one embodiment, the bioactive agent is a growth factor or differentiation factor. For instance, a scaffold for nerve regeneration may include a neurotrophic factor. The implantable scaffold may include a plurality of lipid microtubules or nanoparticles disperse on or among the nanofibers for controlled release of the bioactive agent, or the bioactive agent may, along with the at least one synthetic polymer, form the nanofibers themselves.

In one particular embodiment, a scaffold for tissue regeneration is provided that include (i) at least two layers which include a plurality of uniaxially oriented, polymeric nanofibers, wherein at least 75% of the nanofibers are oriented within 20 degrees of the uniaxial orientation and wherein the layers are stacked and oriented such that the nanofiber orientation of among the layers is substantially identical; (ii) one or more spacers in the stacked layers, between the at least two layers of uniaxially oriented nanofibers, wherein the spacers comprise a hydrogel.

In another aspect, a method is provided for fabricating an implantable scaffold for tissue regeneration, wherein the method includes the steps of (i) electrospinning a polymer to form two or more films of uniaxially oriented nanofibers; and (ii) stacking the two or more uniaxially oriented nanofiber films together to form an oriented, three-dimensional scaffold. This method may further include interposing layers of at least one hydrogel in between the films of uniaxially oriented nanofibers, and/or disposing the oriented, three-dimensional scaffold inside a tubular conduit with the nanofiber orientation substantially aligned in the direction of the axis of the conduit.

In yet another aspect, a method is provided for tissue regeneration that includes the step of implanting one of the scaffold devices described above into a patient at a site in need of tissue regeneration. In a preferred embodiment, the site is between two ends of a nerve in need of regeneration.

BRIEF DESCRIPTION OF THE DRAWINGS

FIG. 5B shows the nanofibers magnified (scale bar=1 μm).

DETAILED DESCRIPTION OF THE PREFERRED EMBODIMENTS

Figure 1:
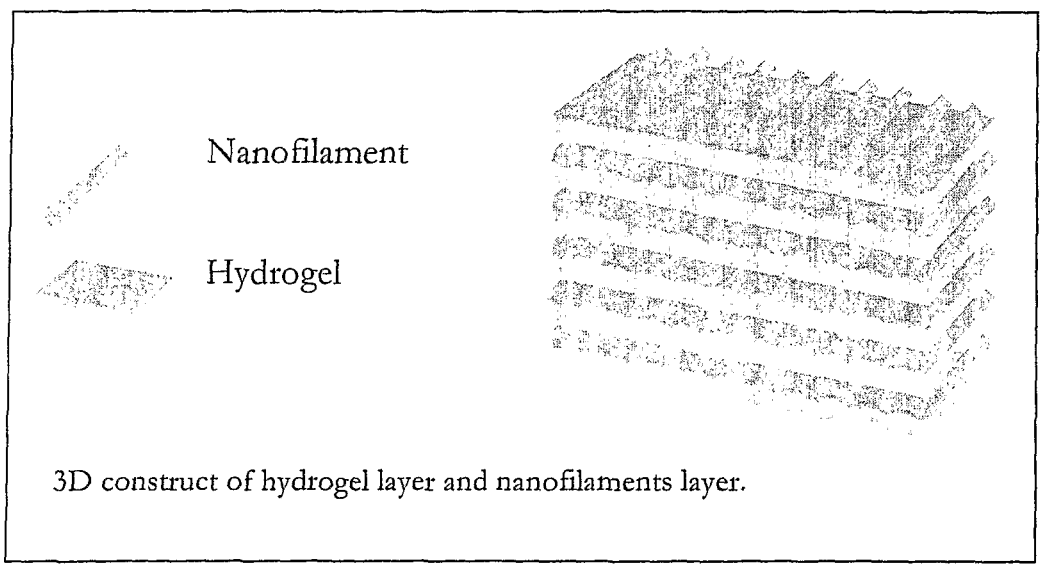
FIG. 1 is a perspective view of a schematic of one embodiment of a tissue scaffold with layers of uniaxially oriented nanofibers alternating with layers of hydrogel.

An improved scaffold for tissue regeneration has been developed that can match the performance of autografts. The scaffold guides cell migration in vitro or in vivo. It can act as a bridging and guidance substrate. It was advantageously discovered that highly aligned fibers promote better growth, and that a gap between layers of fibers further improved the scaffold's performance. The scaffold beneficially provides directional cues for cell and tissue regeneration, presumably by mimicking the natural strategy using filamentous structures during development and regeneration. In the specific case of peripheral nerve regeneration, it is believed that the implantable scaffold of oriented nanofibers described herein aids or substitutes for the fibrin cable/bridge, as well as provides a guide for invasion of growth-promoting Schwann cells into the scaffold. A further advantage is that the performance of the oriented nanofiber scaffold is such that no exogenous trophic/ECM factors may be required to facilitate regeneration across a long nerve gap. That is, the oriented nanofibers guide endogenous supportive cell migration into the injury site, positively influencing regeneration across gaps that otherwise would not regenerate.

Advantageously, the present nanofiber scaffolds are relatively easy to fabricate, handle, store, and sterilize compared to obtaining autografts. Furthermore, they can be made only of synthetic polymer, and avoid complications associated with the use of proteins or cells. In addition, they can be pre-customized (e.g., diameter or length) for different types of nerve injury, and are suitable for sensory, motor and mixed nerve repair. Moreover, unlike conventional tubular conduits, the present nanofiber scaffolds are less dependent on the formation of an initial fibrin cable between proximal and distal nerve stump.

In one aspect, the implantable scaffold includes an anisotropic three-dimensional structure which comprises a plurality of uniaxially oriented nanofibers made of at least one synthetic polymer.

As used herein, the terms "nanofiber" refers to a fiber, strand, fibril, or threadlike structure having a diameter from about 40 nm to about 1500 nm. As used herein, the term "nanofilament" is synonymous with "nanofiber." In a preferred embodiment, the nanofibers have a diameter from about 200 nm to about 1000 nm, more preferably from about 400 nm to about 1000 nm. In one case, the nanofibers have a diameter between 500 and 800 nm.

As used herein, the term "uniaxial orientation" refers to a collection of nanofibers where greater than 50% of the nanofibers are oriented within 40° of an axis, i.e., ±20° of the axis. Importantly, the nanofibers are oriented in the structure over several millimeters in length, e.g., between 2 and 100 mm. In a preferred embodiment, at least 60%, more preferably at least 75%, and still more preferably at least 85%, of the nanofibers are within 20 degrees of the uniaxial orientation.

As used herein, the term "implantable scaffold" means that the scaffold is suitable for use in vivo, i.e., by implantation into a patient in need of tissue regeneration, such as at an injury (or disease) site, to heal neural, cartilage, bone, cardiovascular and/or other tissues. In a preferred embodiment, the scaffold is used in the regeneration of tissues of the peripheral nervous system or the central nervous system. For example, the implantable scaffold can be implanted into an injured sciatic or cavernous nerve, or into a spinal cord or brain site. The term "patient" generally refers to humans or other mammals.

The nanofibers are formed from at least one polymer, which preferably is a synthetic polymer. In a preferred embodiment, the polymer is a biocompatible, thermoplastic polymer known in the art. In one embodiment, the polymer is a polyester or polyamide suitable for use in in vivo applications in humans. The polymer can be biodegradable or non-biodegradable, or may include a mixture of biodegradable and non-biodegradable polymers.

Representative examples of synthetic polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polyalkylenes such as polyethylene and polypropylene, polyalkylene glycols such as poly(ethylene glycol), polyalkylene oxides such as poly(ethylene oxide), polyvinyl alcohols, polyvinyl ethers, polyvinyl esters, polyvinylpyrrolidone, poly(vinyl alcohols), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Examples of preferred biodegradable polymers include polymers of hydroxy acids such as lactic acid and glycolic acid, and copolymers with polyethylene glycol (PEG), polyanhydrides, poly(ortho)esters, poly(butyric acid), poly(valeric acid), poly(lactide-co-caprolactone), blends and copolymers thereof. In a preferred embodiment, the biodegradable polymer nanofibers includes a poly(caprolactone), a poly(lactic-co-glycolic acid), or a combination thereof.

In another embodiment, the non-biodegradable polymer nanofibers includes a poly(acrylonitrile). Non-degradable polymers may be selected for applications where structural support from the scaffold is necessary or where elements such as electrodes or microfluidics are incorporated into the scaffold.

In another embodiment, the nanofibers are formed from at least one natural polymer. Examples of suitable natural polymers include proteins such as albumin, collagen, gelatin, Matrigel, Fibrin, polypeptide or self-assembling peptide based hydrogels, and prolamines, for example, zein, and polysaccharides such as alginate, agarose, cellulose and polyhydroxyalkanoates, for example, polyhydroxybutyrate.

In one embodiment, the structure of the implantable scaffold includes multiple, stacked layers, i.e., films, of the uniaxially oriented nanofibers. In one embodiment, each layer is about 10 μm thick. Thicker or thinner layers may also be used; however, the thickness typically is selected to be one capable of handling and manipulation to stack or otherwise assemble a 3-D scaffold. For example, the film thickness may enable manual handling, such as to facilitate separation from a (temporary) substrate on which the nanofibers are electrospun. Preferably, each layer is oriented such that the nanofiber orientation in the stack is essentially the same. That is, the axial direction of all layers is pointing in substantially the same direction.

Optionally, the stacked structure includes a spacer between some or all of the layers of uniaxially oriented nanofibers. The spacer can provide sufficient openings to permit cells to infiltrate the scaffold and attach to the oriented nanofibers. The spacer may be water soluble or water insoluble, porous or non-porous, preferably is biocompatible, and may be bioerodible/biodegradable. The spacer may have a thickness between about 25 and about 800 μm. In a preferred embodiment, each spacer layer in the stack has a thickness of about 50 to about 250 μm. In a preferred embodiment, the spacer includes a hydrogel, such as a thermo-reversible (i.e., temperature responsive) hydrogel. In one embodiment, the structure consists of alternating layers of oriented nanofibers and layers of a hydrogel or other spacer. See FIG. 1. The hydrogel, for instance, may be an agarose hydrogel or other hydrogel known in the art. In other embodiments, the spacer material may be another gel or gel-like material, such as polyethylene glycol, agarose, alginate, polyvinyl alcohol, collagen, Matrigel, chitosan, gelatin, or combination thereof.

In an alternative embodiment, the uniaxially aligned nanofibers are provided in the structure in a form other than a plurality of layers. For example, the aligned nanofibers may be distributed evenly spaced throughout the three-dimensional structure. In one embodiment, the structure is the result of rolling one layer, i.e., a film, of aligned nanofibers in on itself to form a spiral roll.

The nanofibers structure optionally may be disposed in a secondary structure for containing, positioning, or securing the uniaxially oriented nanofiber structure, and/or for further directing or limiting tissue growth. For example, the secondary structure may be a tubular conduit, in which the nanofiber/spacer structure can be contained and through which a nerve tissue bridge may be grown between two nerve stumps. See FIG. 2. This structure preferably is also made of a biocompatible polymer, preferably one suitable for use in vivo. The polymer may be biodegradable or non-biodegradable, or a mixture thereof. In one embodiment, the secondary structure may be a polysulfone. The secondary structure may be substantially flexible or rigid, depending upon its particular performance needs.

Figure 3:
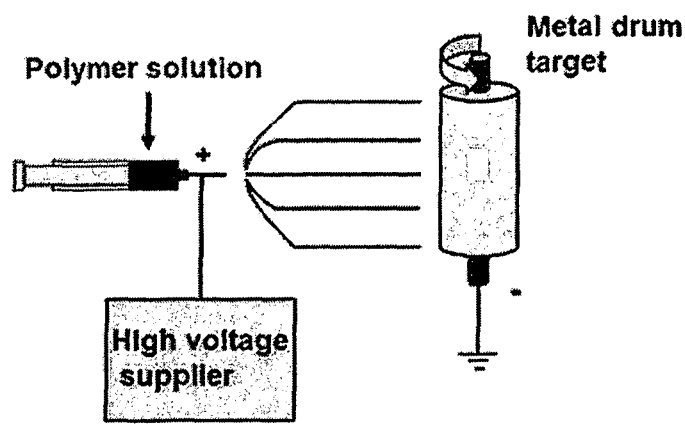
FIG. 3 is schematic showing one embodiment of an electrospinning process for making uniaxially aligned nanofiber films.

The nanofibers may be made by essentially any technique known in the art. In a preferred embodiment, the nanofibers are made using an electrospinning technique, which is well known in the art. See FIG. 3. Essentially any biocompatible polymer that is amenable to electrospinning may be used. The electrospinning equipment may include a rotating drum or other adaptation at the collector end to generate fibers oriented in the millimeter range.

In one embodiment, the implantable scaffold further includes one or more bioactive agents, which may be presented or released to enhance tissue regeneration. As used herein, the term "bioactive agent" refers a molecule that exerts an effect on a cell or tissue. Representative examples of types of bioactive agents include therapeutics, vitamins, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, prostaglandins, immunoglobulins, cytokines, and antigens. Various combination of these molecules can be used. Examples of cytokines include macrophage derived chemokines, macrophage inflammatory proteins, interleukins, tumor necrosis factors. Examples of proteins include fibrous proteins (e.g., collagen, elastin) and adhesion proteins (e.g., actin, fibrin, fibrinogen, fibronectin, vitronectin, laminin, cadherins, selectins, intracellular adhesion molecules, and integrins). In various cases, the bioactive agent may be selected from fibronectin, laminin, thrombospondin, tenascin C, leptin, leukemia inhibitory factors, RGD peptides, anti-TNFs, endostatin, angiostatin, thrombospondin, osteogenic protein-1, bone morphogenic proteins, osteonectin, somatomedin-like peptide, osteocalcin, interferons, and interleukins.

In a preferred embodiment, the bioactive agent includes a growth factor, differentiation factor, or a combination thereof. As used herein, the term "growth factor" refers to a bioactive agent that promotes the proliferation of a cell or tissue. Representative examples of growth factors that may be useful include transforming growth factor-α (TGF-α), transforming growth factor-β (TGF-β), platelet-derived growth factors (PDGF), fibroblast growth factors (FGF), nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), (e.g., TGFs α, β, β1, β2, and β3), any of the bone morphogenic proteins, skeletal growth factor, bone matrix derived growth factors, and bone derived growth factors and mixtures thereof. As used herein the term "differentiation factor" refers to a bioactive agent that promotes the differentiation of cells. Representative examples include neurotrophins, colony stimulating factors (CSF), and transforming growth factors. Some growth factors may also promote differentiation of a cell or tissue. Some differentiation factors also may promote the growth of a cell or tissue. For example, TGF may promote growth and/or differentiation of cells.

The bioactive agent may be incorporated into the scaffold in a variety of different ways. In a preferred embodiment, the bioactive agent is located and/or formulated for controlled release to affect the cells or tissues in or around the oriented nanofiber structures. For instance, it may be dispersed in a controlled release matrix material. In one embodiment, the bioactive agent is provided in lipid microtubules or nanoparticles selected to modulate the release kinetics of the bioactive agent. Such particles may be dispersed among the nanofibers, or provided in or on one or more layers in the scaffold structure. In another embodiment, the bioactive agent is actually integrated into, forms part of, the nanofibers themselves. This may be done, for example, by adding the bioactive agent to a polymer solution prior to electrospinning the solution to form the oriented nanofibers. Release of the bioactive agent may be controlled, at least in part, by selection of the type and amounts of bioerodible or biodegradable matrix materials in the nanoparticles or nanofibers.

In one particular embodiment, the scaffold for tissue regeneration includes at least two layers which comprise a plurality of uniaxially oriented, polymeric nanofibers, wherein at least 75% of the nanofibers are oriented within 20 degrees of the uniaxial orientation and wherein the layers are stacked and oriented such that the nanofiber orientation of among the layers is substantially identical; one or more spacers in the stacked layers, between the at least two layers of uniaxially oriented nanofibers, wherein the spacers comprise a hydrogel.

In another aspect, a method is provided for fabricating an implantable scaffold for tissue regeneration, wherein the method includes the steps of electrospinning a polymer (solution) to form two or more films of uniaxially oriented nanofibers, and stacking the two or more uniaxially oriented nanofiber films together to form an oriented, three-dimensional scaffold. In one embodiment, the method further includes interposing layers of at least one hydrogel or other spacer material in between the films of uniaxially oriented nanofibers. In still another embodiment, the method further includes disposing the oriented, three-dimensional scaffold inside a tubular conduit with the nanofiber orientation substantially aligned in the direction of the axis of the conduit.

The tissue regeneration scaffolds described herein mimic the strategy used by collagen and other fibrillar structures to guide cell migration or tissue development and regeneration in a direction-sensitive manner. In one embodiment, a method of tissue regeneration is provided that includes the step of implanting into a patient an implantable scaffold as described above. In one particular embodiment, the site of implantation is between two nerve stumps in a peripheral nerve. The uniaxially oriented nanofibers of the scaffold promote nerve regeneration by promoting and supporting directional glial and nerve infiltration of the scaffold. Thus, the scaffold can be applied to guide the migration of endogenous or transplanted cells and tissues, including tissues of the peripheral and central nervous system.

The oriented nanofiber structures and methods described herein can be adapted to a variety of tissue regeneration applications, where guided invasion/migration of endogenous or transplanted cells is desired. Each tissue may require different densities of nanofibers for a given volume of scaffold for optimal performance. These parameters could be routinely determined for various tissues. The ability of the oriented nanofiber structures to guide cell migration/process extension also may be useful in seeding of tissue engineering constructs if nanofibers are embedded with/within other isotropic scaffolds. It is envisioned that the oriented nanofiber structures and methods can be applied to the regeneration of cartilage, bone, neural, and cardiovascular tissues. In addition, the oriented nanofiber scaffolds may have other in vivo and ex vivo uses including wound repair, growth of artificial skin, veins, arteries, tendons, ligaments, cartilage, heart valves, organ culture, treatment of burns, and bone grafts.

As used herein, the terms "comprise," "comprising," "include," and "including" are intended to be open, non-limiting terms, unless the contrary is expressly indicated.

The present invention may be further understood with reference to the following non-limiting examples.

EXAMPLE 1

Method of Making Oriented Nanofiber Films by Electrospinning

Figure 5A:
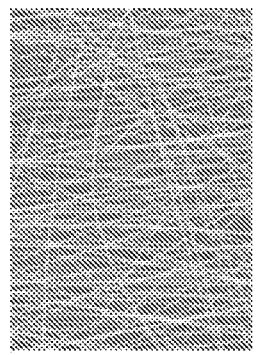
FIGS. 5A-B are scanning electron micrograph images of one embodiment of the uniaxially aligned nanofibers.
Figure 5B:
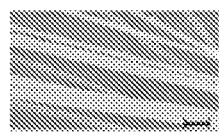
Figure 6:
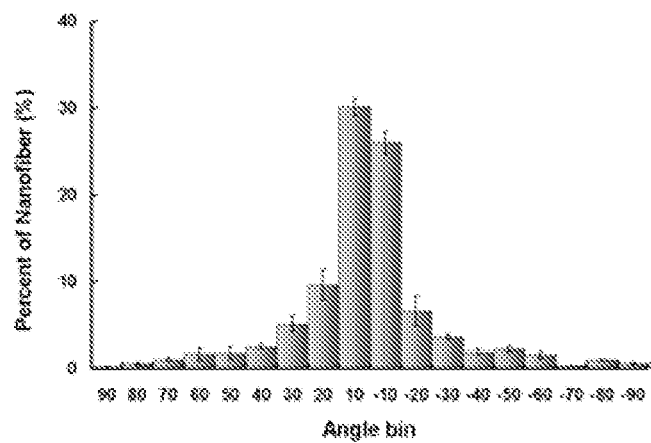
FIG. 6 is a graph illustrating the distribution of nanofiber alignment in one example. More than 75% of all nanofibers fall within 20 degrees of the uniaxial orientation.

Uniaxially oriented nanofiber films were fabricated by electrospinning poly(acrylonitrile-co-methylacrylate, random copolymer, 4 mole percent of methacrylate) (PAN-MA) on a high speed rotating metal drum. An 18% (w/v) PAN-MA solution was prepared in an organic solvent, N,N-Dimethyl Formamide (DMF) at 60° C. The polymer solution was loaded into a 10 mL syringe and delivered at a constant flow rate (1 mL/hour) to a 21 gauge metal needle connected to a high voltage power supply. Upon applying a high voltage power supply of about 13 kV to about 18 kV, a fine jet of polymer solution was ejected from the needle and deposited on a thick aluminum foil wrapped around the high speed rotating metal drum. The foil carrying the aligned electrospun nanofiber film was then removed and stored at room temperature. The nanofiber film was approximately 10 μm thick and composed of nanofibers with diameters in the range of about 400 nm to about 600 nm. See FIGS. 5A-B. The alignment and morphology of the nanofibers were examined using scanning electron microscopy (S-800 SEM, Hitachi) and quantified with Image-Pro software (MediaCybernetics). FIG. 6 is a graph which illustrates the distribution of nanofiber alignment. More than 75% of all nanofibers fall within 20 degrees of the uniaxial orientation.

EXAMPLE 2

Three-Dimensional Oriented Nanofiber Scaffold

Figure 2:
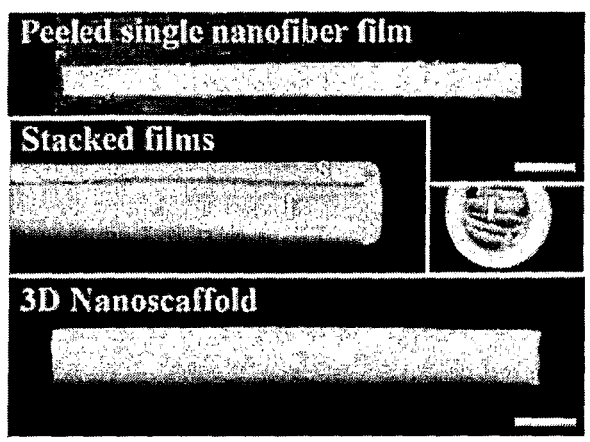
FIG. 2 is a photograph showing different perspectives of one embodiment of an implantable tissue scaffold with layers of uniaxially oriented nanofibers disposed in a tubular conduit.
Figure 4:
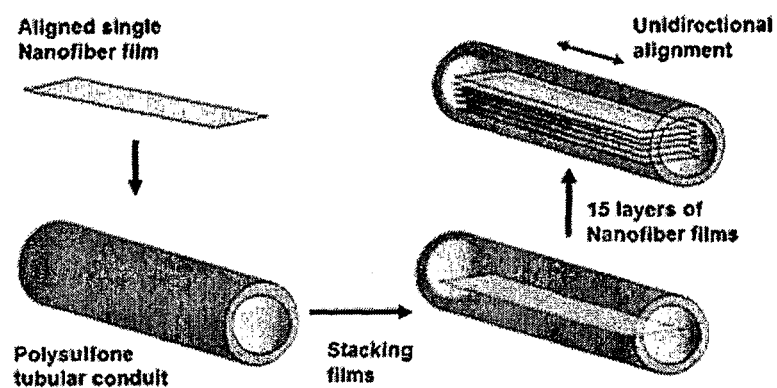
FIG. 4 is a schematic showing one embodiment of a process for assembling an implantable scaffold that includes stacks of uniaxially aligned nanofiber films.

An oriented, 3-D nanofiber scaffold was created by stacking the uniaxially oriented nanofiber films made as described in Example 1. A total of 15 nanofiber films were cut into 17 mm×1 mm pieces, removed from the aluminum foil, and stacked so that the orientation of the nanofibers aligned with the axis of regeneration within two halves of a longitudinally split polysulfone nerve conduit (Koch Membrane Systems, 50,000 MW cutoff—19 mm long, 1.5 mm inner diameter). The longitudinal half-cut was closed and sealed using UV light curing adhesive. See FIG. 4. The nanofiber scaffold was sterilized by soaking it in a 70% ethanol solution for 30 minutes and washing it three times with sterilized deionized water. The nanofiber scaffold was stored in sterilized PBS until implantation. FIG. 2 shows representative photograph of a single nanofiber film, stacked films, and a three-dimensional nanofiber scaffold.

EXAMPLE 3

In Vivo Nerve Tissue Growth Using Oriented, 3-D Nanofiber Scaffold

The nanofiber scaffolds fabricated as described in Example 2 were implanted into a transected tibial nerve of adult male rats. Autograft implants and saline filled nerve conduit implants were also tested in comparator/control animals.

Double immunostaining (axons and Schwann cells) revealed that the implanted nanofiber scaffolds facilitated the regeneration of transected tibial nerves across 17 mm nerve gaps, and that host derived Schwann cells infiltrated the nanofiber scaffolds from both proximal and distal stumps of the nerve. The transected axons entered into the proximal end of the nanofiber scaffolds, regenerated through entire length of the nanofiber scaffold along the nanofiber films, and moved into the distal stump of the nerve. This successful regeneration was observed in all nanofiber scaffold treated animals (n=12). The regenerating axons always co-localized with the aligned Schwann cells through the entire nanofiber scaffold; no regenerated axons were observed without co-localization with the Schwann cells. However, aligned Schwann cell formations without the presence of axons were observed. The regenerated axons and the infiltrated Schwann cells regrew along the aligned nanofiber films, suggesting that the aligned nanofiber films guide the direction of the regenerated axons and the infiltrated Schwann cells after injury akin to the in vitro observations of DRG neurite extension.

In autograft implanted animals, the transected axons entered into the autograft nerve and moved into the distal stump of nerve. Unlike in the regeneration observed through nanofiber scaffolds, regenerated axons within the autograft treated animals were tightly packed in with the aligned Schwann cells, suggesting that the autografts allowed lesser infiltration of non-neuronal cells such as fibroblasts as compared to nanofiber scaffolds.

Unlike with nanofiber scaffolds and autografts, no cellular or extracellular matrix (ECM) structures within the conduit was observed in more than 90% of the saline filled nerve conduit treated animals. Even though a cable structure between proximal and distal nerve stumps was observed in about 10% of the animals, it was thin (i.e., diameter was smaller 50 µm) and stained positive for Collagen type 1, but not for NF160 or S-100. In the 90% of the cases in which the nerve conduit was empty, axons were observed only at the proximal nerve stump along with the Schwann cells, but not in the distal nerve stump. This observation suggests that the saline filled nerve conduits might fail to form the initial fibrin cable between proximal and distal nerve stump due to a long nerve gap (17 mm gap).

Immunostaining for Laminin, RECA-1, and GAP-43 revealed that the infiltrated Schwann cells reorganized into the bands of Bungner along the aligned nanofiber films and blood vessels were reformed through the entire length of the nanofiber scaffolds. Many small and large blood vessels were reformed and, interestingly, some of the blood vessels paralleled the direction of the aligned Schwann cells. Besides blood vessel formation, the bands of Bungner consisting of aligned Schwann cells (infiltrated from both proximal and distal stump of the nerve) and endogenously deposited laminin were consistently observed. Furthermore, the GAP-43 and S-100 double immunostaining confirmed that the axons observed through entire nanofiber scaffold were regenerating or sprouting axons.

The cross-section of the implants revealed that the pattern of nerve regeneration through the nanofiber scaffolds was different from that of both autografts and of normal controls. In the nanofiber scaffolds, the regenerating axons always co-localized with infiltrated Schwann cells, which ensheathed the regenerating axons with myelin through entire scaffold. No axons were observed in the absence of Schwann cells. Unlike with autografts and normal controls, however, non-neuronal cells including macrophages and fibroblasts were observed in axon/Schwann cell depleted areas, suggesting that Schwann cells were not the only cells infiltrating into the implanted nanofiber scaffolds. Most importantly, the pattern of regenerating axons and the infiltrated Schwann cells were guided by the nanofibers. Overlapping immunostained axons with bright field imaged nanofiber films shows that the regenerating axons and Schwann cells grew on or beneath the nanofibers.

Retrograde dye injection into the affected muscle revealed that the motoneuron cell bodies in the spinal cord and their reformed terminals (i.e., neuromuscular junctions) were anatomically reconnected in nanofiber scaffolds and autograft implanted animals, but not in saline filled nerve conduit implanted animals. Positive staining of the motoneurons suggests Fluororuby was picked up by the motoneuron terminals, diffused through the reinnervated nerve and the implanted nanofiber scaffolds and autografts, and accumulated around motoneurons in the spinal cord.

Recordings were taken from mixed, sensory, and motor nerve components of the regenerated nerve in response to tibial nerve, dorsal root, and ventral root stimulation respectively. In mixed and sensory nerves, significantly higher stimulation levels were required to recruit the regenerating axons in autograft and nanofiber scaffold implants as compared to normal animals. However, these regenerating axons were functional (i.e., propagating an action potential) and it is important to note that nanofiber scaffold implants performed comparably to autografts. Interestingly, the threshold levels of stimulation required to form motor neuron induced compound action potential (CAP) were found to be similar between nanofiber scaffold implants and normal animals (no statistical difference). In additional, CAPs recorded from autograft and nanofiber scaffold implanted animals were broader than those recorded from normal control animals. These results suggest a larger composition of smaller diameter axons, a finding that agrees with the measured distribution of axon caliber and the extent of myelination. Recovery of mixed, sensory, and motoneuron conduction after bridging with nanofiber scaffolds or autografts was determined by measuring the time latency from the application of an electrical pulse at the stimulus site to the detection of the resulting CAP at the recording site. Conduction latency in all cases was significantly higher across autografts and nanofiber scaffolds than across normal, unoperated nerves, suggesting that regenerating nerve propagates action potentials more slowly than intact nerve. Comparing autografts and nanofiber scaffolds implants, conduction latency across mixed and sensory nerve was significantly shorter through autografts. However, in motor nerves there was no significant difference in conduction latencies.

Grid walking studies showed significantly fewer foot slips in autograft and nanofiber scaffolds treated animals than in saline filled nerve conduit treated animals. These results suggest that both nanofiber scaffolds implants and autografts result in better functional recovery than saline-filled nerve conduit implants.

In summary, the results indicate that a uniaxially oriented nanofiber scaffold has an equivalent performance to a mixed nerve autograft in 17 mm long nerve gaps without the addition of exogenous trophic or matrix proteins. When implanted across the 17 mm tibial nerve gap, the aligned nanofibers enabled Schwann cell migration and laminin-1 deposition along their length, allowing formation of the bands of Bungner through the entire nanofiber scaffold. Tibial nerve regeneration across the nerve gap was facilitated without the addition of exogenous proteins or cells, such as neurotrophic factors (e.g., nerve growth factor), extracellular matrix molecules (e.g., pre-coated laminin), or Schwann cells. That is, an exclusively synthetic scaffold matched the performance of a mixed nerve autograft in enabling functional regeneration across a long nerve gap.

EXAMPLE 4

Directional Neurite Extension In Vitro

A tissue scaffold was constructed which consisted of multi-layered hydrogel structures embedded with uniaxially oriented electrospun nanofiber monolayers. The nanofibers had diameters of 200 to 500 nm and were made of a mixture of poly(caprolactone) and poly(lactic-co-glycolic acid). The hydrogel was a thermo-reversible agarose hydrogel.

Primary rat derived dorsal root ganglia explants were dissected, seeded into one end of the tissue scaffolds, and cultured for four days. After four days of incubation, the scaffolds were fixed and cryosectioned for immunohistochemical analysis. Neurofilament marker was used to identify axons while S-100 was used to identify Schwann cells.

The results demonstrated that the uniaxially oriented neurite outgrowths of DRG processes were observed through the entire scaffold structure. In addition, the oriented neurite outgrowth was accompanied by aligned Schwann cells. This in vitro test demonstrated that (i) uniaxially oriented nanofibers can direct the neurite outgrowth of axons and (ii) multilayers of alternating hydrogel and nanofibers can provide neurons with a three-dimensional growth environment.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable synthetic scaffold for tissue regeneration comprising:
a scaffold structure comprising (i) a plurality of uniaxially oriented nanofibers oriented within 20 degrees of the uniaxial orientation, the nanofibers consisting essentially of at least one synthetic polymer selected from the group consisting of poly(hydroxyl acids), poly(lactic) acids, polyanhydrides, polyorthoesters, polyamides, polyalkylenes, polyalkylene glycols, polyalkylene oxides, polyvinyl alcohols, polyvinyl ethers, polyvinyl esters, polyvinyl alcohols, poly(butyric acid), polyvinylpyrrolidone, poly(valeric acid), poly(lactide-co-caprolactone), poly(acrylonitrile), derivatives thereof, copolymers thereof, and blends thereof, and (ii) a tubular conduit consisting essentially of a synthetic polymer, the nanofibers being disposed within an annular channel defined by and within the tubular conduit,
wherein the scaffold structure is effective to guide cell migration in vitro or in vivo without requiring exogenous trophic or extracellular matrix factors.

2. The implantable scaffold of claim 1, wherein the nanofibers have a diameter between about 400 nm and about 800 nm.

3. The implantable scaffold of claim 1, wherein the scaffold structure comprises two or more stacked layers of uniaxially oriented nanofibers, the layers being oriented such that the nanofiber orientation among the layers is substantially identical.

4. The implantable scaffold of claim 3, wherein the scaffold structure includes a spacer between layers of uniaxially oriented nanofibers in the stacked layers.

5. The implantable scaffold of claim 4, wherein the spacer has a thickness between 50 and 100 μm.

6. The implantable scaffold of claim 4, wherein the spacer comprises a hydrogel, polyethylene glycol, agarose, alginate, polyvinyl alcohol, collagen, Matrigel, chitosan, gelatin, or a combination thereof.

7. The implantable scaffold of claim 6, wherein the scaffold comprises alternating layers of oriented nanofibers and layers of hydrogel.

8. The implantable scaffold of claim 1, wherein the tubular conduit comprises a non-biodegradable polymer.

9. The implantable scaffold of claim 1, wherein the tubular conduit comprises a polysulfone.

10. The implantable scaffold of claim 1, wherein the synthetic polymer of the nanofibers is a synthetic biodegradable polymer selected from the group consisting of a poly(caprolactone), a poly(lactic-co-glycolic acid), and a combination thereof.

11. The implantable scaffold of claim 1, wherein the synthetic polymer of the nanofibers is a synthetic non-biodegradable polymer.

12. The implantable scaffold of claim 11, wherein the synthetic non-biodegradable polymer comprises a poly(acrylonitrile).

13. The implantable scaffold of claim 1, wherein the scaffold is an anisotropic three-dimensional structure which provides directional cues to promote cell and tissue growth in the structure.

14. The implantable scaffold of claim 13, wherein the anisotropic three-dimensional structure is effective to guide the ingrowth of cells into the structure.

15. The implantable scaffold of claim 14, wherein the three-dimensional structure is effective to guide the ingrowth of Schwann cells.

16. The implantable scaffold of claim 13, wherein the anisotropic three-dimensional structure is effective to guide the direction of axon regeneration and the infiltration of Schwann cells; and
wherein the tubular conduit in which the anisotropic three-dimensional structure is disposed is suited for placement between two nerve stumps.

17. A scaffold for tissue regeneration comprising:
at least two layers which consist essentially of a plurality of uniaxially oriented, polymeric nanofibers, wherein at least 75% of the nanofibers are oriented within 20 degrees of the uniaxial orientation and wherein the layers are stacked and oriented such that the nanofiber orientation of the layers is substantially identical;
one or more spacers disposed between the at least two layers of uniaxially oriented nanofibers,
wherein the polymeric nanofibers are made of a synthetic polymer selected from the group consisting of poly(hydroxyl acids), poly(lactic) acids, polyanhydrides, polyorthoesters, polyamides, polyalkylenes, polyalkylene glycols, polyalkylene oxides, polyvinyl alcohols, polyvinyl ethers, polyvinyl esters, polyvinyl alcohols, poly(butyric acid), polyvinylpyrrolidone, poly(valeric acid), poly(lactide-co-caprolactone), poly(acrylonitrile), derivatives thereof, copolymers thereof, and blends thereof, and
wherein the at least two layers of uniaxially oriented nanofibers are effective to guide cell migration in vitro or in vivo without requiring exogenous trophic or extracellular matrix factors.

18. The scaffold of claim 17, wherein the one or more spacers comprise a hydrogel, polyethylene glycol, agarose, alginate, polyvinyl alcohol, collagen, Matrigel, gelatin, or a combination thereof.

19. A method for fabricating an implantable scaffold for tissue regeneration, the method comprising the steps of:
    electrospinning at least one synthetic polymer to form two or more films of uniaxially oriented nanofibers, wherein the nanofiber films consist essentially of uniaxially oriented synthetic nanofibers and the at least one synthetic polymer is selected from the group consisting of poly(hydroxyl acids), poly(lactic) acids, polyanhydrides, polyorthoesters, polyamides, polyalkylenes, polyalkylene glycols, polyalkylene oxides, polyvinyl alcohols, polyvinyl ethers, polyvinyl esters, polyvinyl alcohols, poly(butyric acid), polyvinylpyrrolidone, poly(valeric acid), poly(lactide-co-caprolactone), poly(acrylonitrile), derivatives thereof, copolymers thereof, and blends thereof; and
    stacking the two or more uniaxially oriented nanofiber films together to form a three-dimensional scaffold; and
    disposing the oriented, three-dimensional scaffold inside a tubular conduit with the nanofiber orientation of the nanofiber films being substantially aligned in the direction of the axis of the conduit,
    wherein the scaffold is effective to guide cell migration in vitro or in vivo without requiring exogenous trophic or extracellular matrix factors.

20. The method of claim 19, further comprising interposing layers of at least on hydrogel in between the films of uniaxially oriented nanofibers.

21. A method of tissue regeneration comprising:
    implanting into a patient the implantable scaffold of claim 1 at a site in need of tissue regeneration.

22. The method of claim 21, wherein the site is between two ends of a nerve in need of regeneration.

23. A method for regenerating nerve tissue in a mammal, comprising:
    implanting in a mammal the implantable scaffold of claim 16, in a gap between two stump ends of a transected nerve in the mammal;
    securing a first end of the tubular conduit about one of the nerve stumps; and
    securing an opposed second end of the tubular conduit about the second nerve stump; and
    allowing axons from the nerve stumps to regenerate and Schwann cells to infiltrate into the tubular conduit.

* * * * *